United States Patent [19]

Wehinger et al.

[11] Patent Number: 4,565,824

[45] Date of Patent: Jan. 21, 1986

[54] CERTAIN NITRATOALKYL ESTER DIHYDROPYRIDINES HAVING ANTIHYPERTENSIVE PROPERTIES

[75] Inventors: Egbert Wehinger; Horst Meyer; Stanislav Kazda; Andreas Knorr, all of Wuppertal, Fed. Rep. of Germany

[73] Assignee: Bayer Aktiengesellschaft, Leverkusen, Fed. Rep. of Germany

[21] Appl. No.: 550,321

[22] Filed: Nov. 9, 1983

[30] Foreign Application Priority Data

Nov. 30, 1982 [DE] Fed. Rep. of Germany ........ 3244178

[51] Int. Cl.$^4$ ................. C07D 211/90; A61K 31/455
[52] U.S. Cl. .................................. 514/356; 546/318; 546/321
[58] Field of Search ..................... 546/321, 318, 316; 424/266; 514/356

[56] References Cited

U.S. PATENT DOCUMENTS 4,048,171  9/1977  Bossert et al. ................... 546/321
4,285,955  8/1981  Wehinger et al. ................ 546/321
4,472,411  9/1984  Hatayama et al. ................ 546/321

FOREIGN PATENT DOCUMENTS 0092936  11/1983  European Pat. Off. .

OTHER PUBLICATIONS

Schramm, M. et al., "Novel Dihydropyridines with Positive Inotropic Action" Nature, vol. 303, (Jun. 9, 1983), pp. 535–537.

Bossert, F. et al., "4-Aryldihydropyridines" Angew. Chem. Int. Ed. Engl. 20 (1981), pp. 762–769.

Primary Examiner—Henry R. Jiles
Assistant Examiner—Dale A. Bjorkman
Attorney, Agent, or Firm—Sprung, Horn, Kramer & Woods

[57] ABSTRACT

Dihydropyridines of the formula

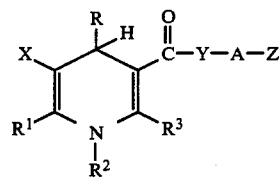

in which

R is aryl or heterocyclic,
$R^1$, $R^2$ and $R^3$ each is hydrogen or various organic radicals,
Y is oxygen, or optionally substituted —NH—,
Z is —O—NO$_2$ or —O—NO,
X is —COR$^4$, —COOR$^5$ or —CO—Y—A—Z,
$R^4$ is alkyl, phenyl, benzyl or an amino radical, and
$R^5$ is an organic radical, or pharmaceutically acceptable acid addition salts thereof, exhibit circulation active properties, e.g. they can be used as antihypertensives, as peripheral and cerebral vasodilators and as coronary therapeutics.

16 Claims, No Drawings

CERTAIN NITRATOALKYL ESTER DIHYDROPYRIDINES HAVING ANTIHYPERTENSIVE PROPERTIES

The present invention relates to 1,4-dihydropyridine derivatives, several processes for their preparation and their use in medicaments, in particular in agents which influence the circulation.

It has already been disclosed that diethyl 1,4-dihydro-2,6-dimethyl-4-phenylpyridine-3,5-dicarboxylate is obtained when ethyl 2-benzylideneacetoacetate is reacted with ethyl β-aminocrotonate or ethyl acetoacetate and ammonia (E. Knoevenagel, Ber. dtsch. chem. Ges. 31, 743 (1898)).

It is also known that certain 1,4-dihydropyridines have interesting pharmacological properties (F. Bossert, W. Vater, Naturwissenschaften 58, 578 (1971)).

It is likewise known from German Offenlegungsschrift (German Published Specification) No. 2,847,236 that similar compounds can be used as coronary agents and as hypotensive agents.

The present invention relates to 1,4-dihydropyridines with substituted carboxylic acid groups, of the general formula (I)

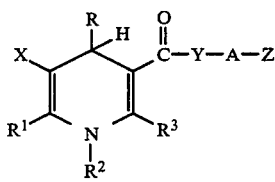

in which

R represents aryl, thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, quinolyl, isoquinolyl, quinazolyl or quinoxalyl, the aryl radical and the heterocyclic radicals optionally containing 1 or 2 identical or different substituents from the group comprising phenyl, alkyl, alkoxy, alkylene, dioxyalkylene, halogen, trifluoromethyl, polyfluoroalkoxy, nitro, cyano, azido and $SO_m$-alkyl (m=0 to 2), $R^1$ and $R^3$ are identical or different and each represents hydrogen, a straight-chain or branched alkyl radical, an aryl radical or an aralkyl radical, $R^2$ denotes hydrogen or a straight-chain or branched alkyl radical, which is optionally interrupted in the alkyl chain by one or two oxygen atoms, or an aryl or aralkyl radical, Y represents an oxygen atom or a nitrogen atom, in which case a hydrogen atom, a lower alkyl radical, an aryl or aralkyl radical or the group —A-Z is also bonded to the nitrogen atom, A represents a straight-chain, branched or cyclic alkylene group which has up to 12 carbon atoms and is optionally substituted by a pyridyl or phenyl group, which can in turn be substituted by halogen, cyano, dialkylamino, alkyl, alkoxy, trifluoromethyl or nitro, Z represents —O—NO$_2$ or —O—NO and X represents the group —COR$^4$, wherein R$^4$ denotes optionally substituted alkyl, aryl, aralkyl or anilino or an amino, monoalkylamino or dialkylamino group, the alkyl groups optionally forming, with the nitrogen atom, a 5-membered to 7-membered ring which can contain an oxygen or sulphur atom as a further hetero-atom, or X represents the group —COOR$^5$, wherein R$^5$ represents a straight-chain, branched or cyclic, saturated or unsaturated hydrocarbon radical, which is optionally interrupted in the chain by an oxygen or sulphur atom, and/or which is optionally substituted by halogen, cyano, hydroxyl, acyloxy or a phenyl, phenoxy, phenylthio or phenylsulphonyl group, which can in turn be further substituted by halogen, cyano, dialkylamino, alkoxy, alkyl, trifluoromethyl or nitro, or optionally by an α-, β- or γ-pyridyl group, or optionally by an amino group, this amino group carrying two identical or different substituents from the group comprising alkyl, alkoxyalkyl, aryl and aralkyl, and these substituents optionally forming, with the nitrogen atom, a 5-membered to 7-membered ring, which can contain, as a further hetero-atom, an oxygen or sulphur atom or the N-alkyl grouping, or X represents the group —CO—Y'—A'—Z', this group being identical to or different from —CO—Y—A—Z and the definitions of Y', A' and Z' corresponding to those of Y, A and Z, and pharmaceutically acceptable acid addition salts thereof.

The substituents in formula (I) preferably have the following meanings:

R phenyl, naphthyl or thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, quinolyl, isoquinolyl, quinazolyl or quinoxalyl, it being possible for the ring systems mentioned in each case to be substituted by 1 or 2 identical or different substituents from the group comprising phenyl, straight-chain or branched alkyl with 1 to 8 carbon atoms, cycloalkyl with 3 to 7 carbon atoms, alkoxy with 1 to 4 carbon atoms, tri-, tetra- and pentamethylene, dioxymethylene, halogen, trifluoromethyl, trifluoromethoxy, difluoromethoxy, tetrafluoroethoxy, nitro, cyano, azido or $SO_m$—alkyl, m denoting a number from 0 to 2 and alkyl preferably containing 1 to 4 carbon atoms, $R^1$ and $R^3$, which can be identical or different, hydrogen, a straight-chain or branched alkyl radical with 1 to 4, in particular 1 or 2, carbon atoms, a phenyl radical or an aralkyl radical, in particular a benzyl radical, $R^2$ a hydrogen atom or a straight-chain or branched alkyl radical with 1 to 8 carbon atoms, the alkyl radical optionally being interrupted in the alkyl chain by an oxygen atom, or a phenyl radical or a benzyl radical, Y an oxygen atom or a nitrogen atom, in which case a hydrogen atom or an alkyl group with up to 8 carbon atoms or a phenyl or benzyl radical or the group —A-Z is additionally bonded to the nitrogen atom, A a straight-chain, branched or cyclic alkylene radical with up to 12 carbon atoms, in particular up to 6 carbon atoms, which is optionally substituted by an α-, β- or γ-pyridyl group or by a phenyl group, which can in turn be at most trisubstituted by identical or different substituents from the group comprising halogen, in particular fluorine, chlorine and bromine, and cyano, nitro, alkyl, alkoxy and dialkylamino with in each case 1 to 4 carbon atoms per alkyl group, and trifluoromethyl, Z —O—NO$_2$ or —O—NO and X the group —COR$^4$, wherein R$^4$ represents a straight-chain or branched alkyl radical with 1 to 4 carbon atoms, a phenyl radical, a benzyl radical, an anilino radical, an amino group or a monoalkylamino or dialkylamino group with up to 4 carbon atoms per alkyl group, the alkyl groups optionally forming, with the nitrogen atom, a 5- to 7-membered ring, which can contain, as a further hetero-atom, an oxygen or sulphur atom, or X the group —COOR$^5$, wherein R$^5$ represents a straight-chain, branched or cyclic, saturated or unsaturated hydrocarbon radical which has up to 20 carbon atoms and is optionally interrupted in the chain by an oxygen atom or a sulphur atom and/or is optionally substituted by halogen, cyano, hydroxyl or acyloxy, or by a phenyl, phenoxy, phenylthio or phenylsulphonyl group which is optionally substituted by halogen, in particular fluorine, chlorine or bromine, cyano, dialkylamino with in each case 1 or 2 carbon atoms per alkyl group, alkoxy with 1 to 4 carbon atoms, alkyl with 1 to 4 carbon atoms, trifluoromethyl or nitro, or by an α-, β- or γ-pyridyl group, or by an amino group, this amino group carrying two identical or different substituents from the group comprising alkyl with up to 4 carbon atoms, alkoxyalkyl with up to 4 carbon atoms, phenyl and aralkyl, in particular benzyl, and these substituents optionally forming, with the nitrogen atom, a 5-membered to 7-membered ring, which can contain, as a further hetero-atom, an oxygen or sulphur atom or the N-alkyl grouping, the alkyl group preferably containing 1 to 3 carbon atoms, or X the group —CO—Y'—A'—Z', this group being identical to or different from —CO—Y—A—Z and the definition of Y', A' and Z' corresponding to that of Y, A and Z.

The substituents in formula (I) particularly preferably having the following meaning:

R is pyridyl, benzoxadiazolyl or phenyl, mono- or disubstituted by nitro, trifluoromethyl, halogen (fluorine and/or chlorine—identical or different), cyano or azido, R$^1$ and R$^3$ are identical or different and are C$_1$-C$_4$—, in particular C$_1$-C$_2$-alkyl or benzyl, R$^2$ is hydrogen, C$_1$-C$_4$-alkyl or benzyl, Y is 0, A is C$_1$-C$_4$-alkylene, Z is —ONO$_2$ and X is —COR$^4$, in which R$^4$ is C$_1$-C$_4$-alkyl, or X is —COOR$^5$, in which R$^5$ is benzyl or C$_1$-C$_{12}$-alkyl, optionally interrupted in the chain by an oxygen atom, or optionally substituted by halogen (fluorine and/or chlorine—identical or different) and/or by amino, the amino group carrying two identical or different substituents from the group comprising C$_1$-C$_4$-alkyl and benzyl, or X is —CO—Y'—A'—Z', this group being identical to or different from —CO—Y—A—Z and the definitions of Y', A' and Z' corresponding to that of Y, A and Z.

In particular, the substituents in formula (I) have the following meanings:

R is nitrophenyl or trifluoromethylphenyl,

R$_1$ and R$_3$ are methyl,

R$_2$ is hydrogen,

Y is oxygen,

A is C$_1$-C$_3$-alkylene,

Z is —ONO$_2$ and

X is —COR$^4$, in which

R$^4$ is methyl, or

X is —COOR$^5$, in which

R$^5$ is C$_1$-C$_{12}$-alkyl, optionally interrupted in the chain by an oxygen atom, or benzyl.

It has furthermore been found that the 1,4-dihydropyridine derivatives of the general formula (I) are obtained by a process in which (A) ylidene compounds of the formula II

in which

R, R$^1$ and X have the abovementioned meaning, are reacted with enaminocarboxylic acid derivatives of the formula III

in which

R$^2$, R$^3$, Y, A and Z have the abovementioned meaning, if appropriate in the presence of inert organic solvents, or (B) ylidene compounds of the formula II

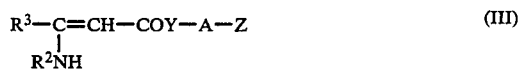

in which

R, R$^1$ and X have the abovementioned meaning, are reacted with amines of the formula (IV) and β-ketocarboxylic acid derivatives of the formula V

R$_2$—NH$_2$     (IV)

R$^3$—CO—CH$_2$—COY—A—Z     (V)

in which

R$^2$, R$^3$, Y, A and Z have the abovementioned meaning, if appropriate in the presence of inert organic solvents, or (C) ylidene-β-dicarbonyl compounds of the formula VI

in which

R, R³, Y, A and Z have the abovementioned meaning, are reacted with enamino compounds of the formula VII

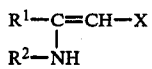 (VII)

in which

R¹, R² and X have the abovementioned meaning, if appropriate in the presence of inert organic solvents, or (D) ylidene-β-dicarbonyl compounds of the formula VI

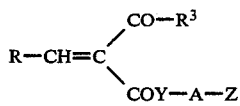 (VI)

in which

R, R³, Y, A and Z have the abovementioned meaning, are reacted with amines of the formula IV and keto derivatives of the formula VIII

 (IV)

 (VIII)

in which

R², R¹ and X have the abovementioned meaning, if appropriate in the presence of inert organic solvents, or (E) aldehydes of the formula IX

 (IX)

in which

R has the abovementioned meaning, are reacted with enamino compounds of the formula VII

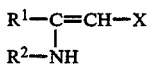 (VII)

in which

R¹, R² and X have the abovementioned meaning, and β-ketocarboxylic acid derivatives of the formula V

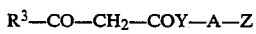 (V)

in which

R³, Y, A and Z have the abovementioned meaning, if appropriate in the presence of inert organic solvents, or (F) aldehydes of the formula IX

 (IX)

in which

R has the abovementioned meaning, are reacted with enaminocarboxylic acid derivatives of the formula III

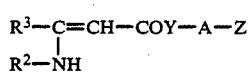 (III)

in which

R², R³, Y, A and Z have the abovementioned meaning, and keto derivatives of the formula VIII

 (VIII)

in which

R¹ and X have the abovementioned meaning, if appropriate in the presence of inert organic solvents, or (G) a group L in 1,4-dihydropyridine derivatives of the formula X

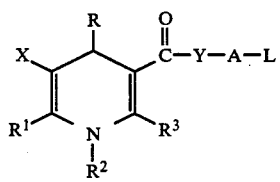 (X)

in which

R, R¹, R², R³, A, X and Y have the abovementioned meaning and

L represents a suitable leaving group, for example, halogen, is replaced by the radical —O—NO₂ or —O—NO.

The salts of the compounds of the formula I can be obtained in a simple manner by customary salt formation methods, for example by dissolving the base and adding the acid, for example hydrogen chloride, and they are isolated in a known manner, for example by filtration, and if necessary purified.

The 1,4-dihydropyridine derivatives according to the invention have valuable pharmacological properties. On the basis of their influencing action on the circulation, they can be used as antihypertensive agents, as peripheral and cerebral vasodilators and as coronary therapeutics, and are thus to be regarded as an enrichment of pharmacy.

The synthesis of the compounds according to the invention can be represented by the following equation, depending on the nature of the starting substances used, methyl 2-nitro-oxyethyl 1,4-dihydro-2,6-dimethyl-4-(3-nitrophenyl)-pyridine-3,5-dicarboxylate being chosen as the example:

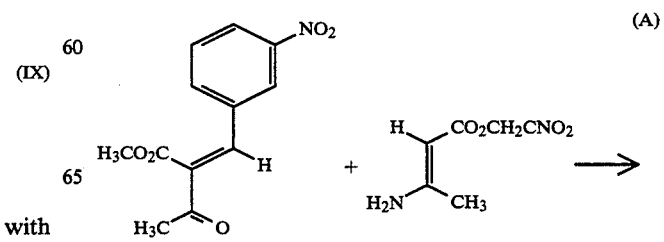 (A)

-continued
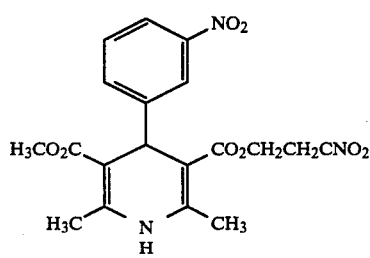
(B)
-continued
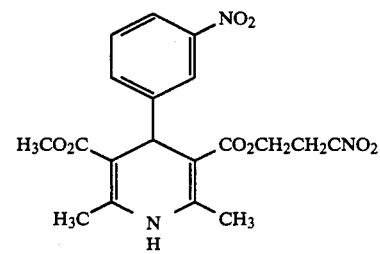
(E)
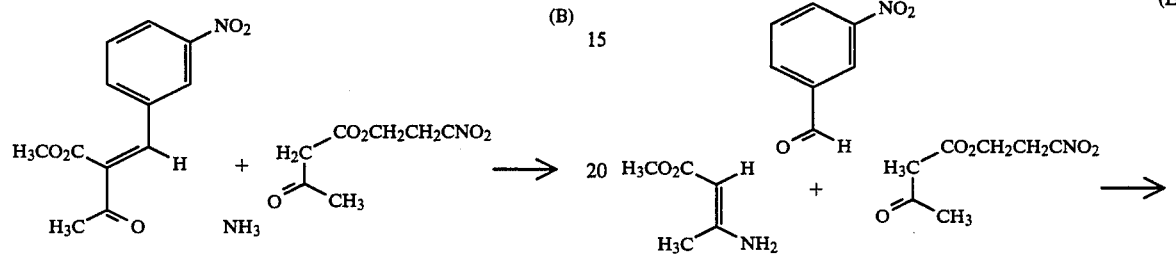
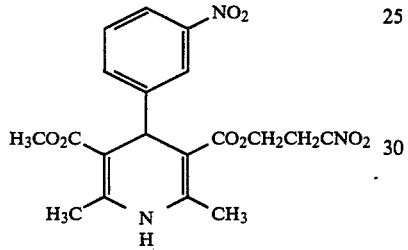
(C)
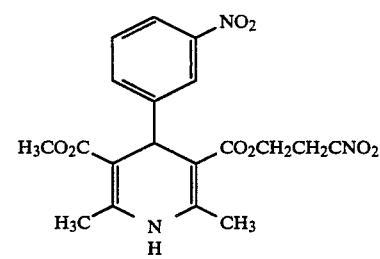
(F)
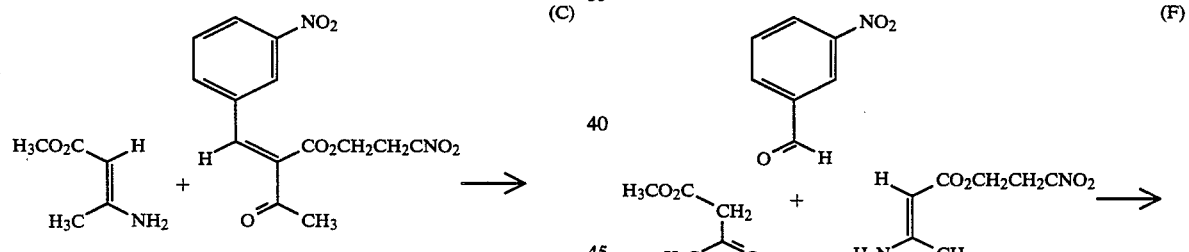
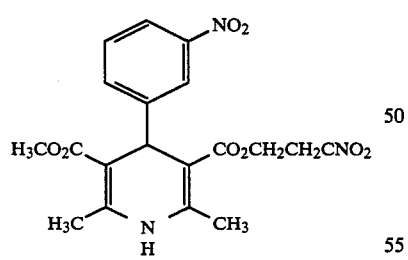
(D)
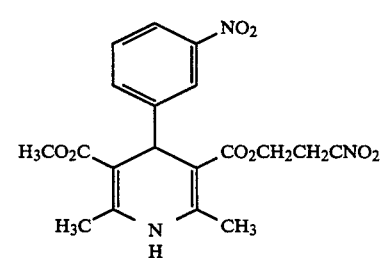
(G)
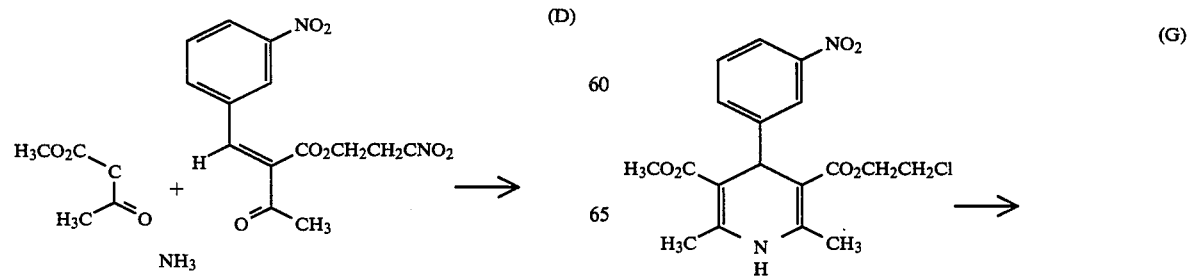

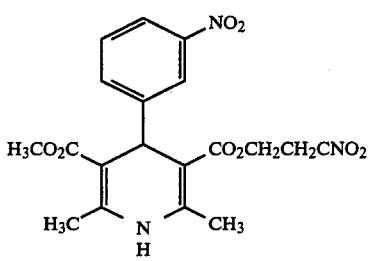

Process variants A and C

According to processes A and C, an ylidene compound of the formula II

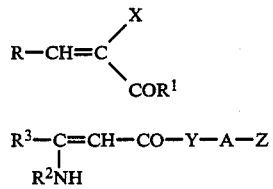

$$R^3-C=CH-CO-Y-A-Z \quad (III)$$
$$\quad | \quad$$
$$R^2NH$$

is reacted with an enaminocarboxylic acid derivative of the formula III, or an ylidene compound of the formula VI

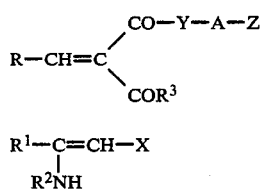

$$R^1-C=CH-X \quad (VII)$$
$$\quad | \quad$$
$$R^2NH$$

is reacted with an enamino compound of the formula VII.

The ylidene compounds of the formula II or of the formula VI used as starting substances are known from the literature, or they can be prepared by methods which are known from the literature (compare, for example, G. Jones "The Knoevenagel Condensation" in Org. Reactions, Volume XV, 204 et seq. (1967)).

Examples which may be mentioned are: benzylideneacetylacetone, β,β-dibenzoylstyrene, 2′-nitrobenzylideneacetylacetone, 3′-nitrobenzylideneacetoacetanilide, 3′-nitrobenzylideneacetoacetamide, 3′-nitrobenzylideneacetoacetic acid dimethylamide, 3′-nitrobenzylideneacetoacetic acid piperidide, methyl 2′-nitrobenzylideneacetoacetate, decyl 3′-nitrobenzylideneacetoacetate, isopropyl 2′-trifluoromethylbenzylideneacetoacetate, cyclopentyl 2′-cyanobenzylideneacetoacetate, 2-methoxyethyl 2′-chlorobenzylideneacetoacetate, 2-cyanoethyl 2′-methoxybenzylideneacetoacetate, benzyl 2′-methylbenzylideneacetoacetate, pyrid-2-ylmethyl 3′-nitrobenzylideneacetoacetate, 2-(N-benzyl-N-methylamino)-ethyl 3′-nitrobenzylideneacetoacetate, 2-nitro-oxyethyl 3′-nitrobenzylideneacetoacetate, 2-nitro-oxyethyl 2′,3′-dichlorobenzylideneacetoacetate, 2-nitroso-oxyethyl 2′,3′-dichlorobenzylideneacetoacetate, methyl α-acetyl-β-(pyrid-3-yl)-acrylate, 2-nitro-oxyethyl α-acetyl-β-(pyrid-3-yl)-acrylate, 2-nitro-oxyethyl α-acetyl-β-(quinolin-4-yl)-acrylate, 2-nitro-oxyethyl α-acetyl-β-(benzoxadiazol-4-yl)-acrylate, 3′-nitrobenzylideneacetoacetic acid (2-nitro-oxyethyl)-amide, 2′,3′-dichlorobenzylideneacetoacetic acid (2-nitro-oxyethyl)-amide and α-acetyl-β-(benzoxadiazol-4-yl)-acetoacetic acid (2-nitro-oxyethyl)-amide.

The enaminocarboxylic acid derivatives of the formula III and of the formula VII used as starting substances are known from the literature, or they can be prepared by methods which are known from the literature (compare A. C. Cope, J. Amer. Chem. Soc. 67, 1017 (1945)).

Examples which may be mentioned are: 4-amino-3-penten-2-one, 3-amino-1,3-diphenylacrolein, β-aminocrotonamide, β-aminocrotonic acid n-butylamide, β-aminocrotonic acid dimethylamide, β-aminocrotonic acid anilide, β-aminocrotonic acid (2-nitro-oxyethyl)-amide, methyl β-aminocrotonate, decyl β-aminocrotonate, 2,2,2-trifluoroethyl β-aminocrotonate, 2-methoxyethyl β-aminocrotonate, 2-phenoxyethyl β-aminocrotonate, benzyl β-aminocrotonate, 2-(N-benzyl-N-methylamino)-ethyl β-aminocrotonate, 2-nitro-oxyethyl β-aminocrotonate and 3-nitro-oxypropyl β-aminocrotonate.

Possible diluents are all the inert organic solvents. These include, preferably, alcohols, such as ethanol, methanol and isopropanol, ethers, such as dioxane, diethyl ether, tetrahydrofuran, glycol monomethyl ether and glycol dimethyl ether, and dimethylformamide, dimethyl sulphoxide, acetonitrile, pyridine and hexamethylphosphoric acid triamide.

The reaction temperatures can be varied within a substantial range. In general, the reaction is carried out between 20° C. and 150° C., preferably between 20° and 100° C., and in particular at the boiling point of the particular solvent.

The reaction can be carried out under normal pressure, but also under increased pressure. In general, it is carried out under normal pressure.

In carrying out the process according to the invention, one mol of the ylidene compound is reacted with one mol of enaminocarboxylic acid derivative in a suitable solvent. The substances according to the invention are preferably isolated and purified by distilling off the solvent in vacuo and recrystallizing the resulting residue from a suitable solvent or subjecting it to one of the customary purification methods, such as, for example, column chromatography on suitable carrier materials.

Process variants B and D

According to processes B and D, an ylidene compound of the formula II is reacted with amines of the formula IV and β-ketocarboxylic acid derivatives of the formula V

$$R^2NH_2 \quad (IV)$$

$$R^3-CO-CH_2-CO-Y-A-Z \quad (V)$$

or an ylidene compound of the formula VI is reacted with amines of the formula IV and β-keto derivatives of the formula VIII

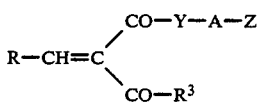

$$R-CH=C\begin{matrix}CO-Y-A-Z\\CO-R^3\end{matrix} \qquad (VI)$$

$$R^2-NH_2 \qquad (IV)$$

$$R^1CO-CH_2-X \qquad (VIII)$$

In the formulae II, IV, V, VI and VIII, the radicals R, $R^1$, $R^2$, $R^3$, Y, A, Z and X have the abovementioned meaning.

Examples of the ylidene compounds of the formula II and of the formula VI used as starting substances have already been given under process variants A and C.

The amines of the formula IV which can be used according to the invention are already known.

Examples which may be mentioned are: ammonia, methylamine, n-butylamine, isobutylamine, β-methoxyethylamine, benzylamine and aniline.

The β-keto derivatives of the formula V and of the formula VIII used as starting substances are already known from the literature, or they can be prepared by methods which are known from the literature (for example D. Borrmann, "Umsetzung von Diketen mit Alkoholen, Phenolen und Mercaptanen" ("Reaction of diketenes with alcohols, phenols and mercaptans"), in Houben-Weyl, Methoden der Organischen Chemie (Methods of Organic Chemistry), Volume VII/4, 230 et seq. (1968); Y. Oikawa, K. Sugano and O. Yonemitsu, J. Org. Chem. 43, 2087 (1978)).

Examples which may be mentioned are: acetylacetone, methyl acetoacetate, decyl acetoacetate, cyclopentyl acetoacetate, 2,2,2-trifluoroethyl acetoacetate, 2-methoxyethyl acetoacetate, 2-phenoxyethyl acetoacetate, benzyl acetoacetate, 2-(N-benzyl-N-methylamino)-ethyl acetoacetate, acetoacetamide, acetoacetanilide, acetoacetic acid dimethylamide, 2-nitro-oxyethyl acetoacetate, 3-nitro-oxypropyl acetoacetate and acetoacetic acid (2-nitro-oxyethyl)-amide.

Possible diluents are all the inert organic solvents. These include, preferably, alcohols, such as ethanol, methanol and isopropanol, ethers, such as dioxane, diethyl ether, tetrahydrofuran, glycol monomethyl ether and glycol dimethyl ether, and dimethylformamide, dimethylsulphoxide, acetonitrile, pyridine and hexamethylphosphoric acid triamide.

The reaction temperatures can be varied within a substantial range. In general, the reaction is carried out between 20° and 150° C., but preferably at the boiling point of the particular solvent.

The reaction can be carried out under normal pressure, but also under increased pressure. In general, it is carried out under normal pressure.

In carrying out the process according to the invention, the substances participating in the reaction are in each case used in molar amounts.

Process variants E and F

According to processes E and F, an aldehyde of the formula IX is reacted with an enamino compound of the formula VII and a β-ketocarboxylic acid derivative of the formula V

$$R-C\begin{matrix}H\\\\O\end{matrix} \qquad (IX)$$

$$R^1-C=CH-X \qquad (VII)$$
$$R^2NH$$

$$R^3-CO-CH_2-CO-Y-A-Z \qquad (V)$$

or an aldehyde of the formula IX is reacted with an enaminocarboxylic acid derivative of the formula III and a β-keto derivative of the formula VIII

$$R-C\begin{matrix}H\\\\O\end{matrix} \qquad (IX)$$

$$R^3-C=CH-CO-Y-A-Z \qquad (III)$$
$$R^2NH$$

$$R^1-CO-CH_2-X \qquad (VIII)$$

In the formulae IX, VII, V, III and VIII, the radicals R, $R^1$, $R^2$, $R^3$, Y, A, Z and X have the abovementioned meaning.

Examples of the enamino compounds of the formula VII and of the formula III used as starting substances and of the β-keto derivatives of the formula V and of the formula VIII have already been given above.

The aldehydes of the formula IX which can be used according to the invention are known from the literature or they can be prepared 6y methods which are known from the literature (compare, for example, E. Mosettig, Org. Reactions VIII, 218 et seq. (1954)).

Examples which may be mentioned are: benzaldehyde, 2-, 3- or 4-phenylbenzaldehyde, α- or β-naphthylaldehyde, 2-, 3- or 4-methylbenzaldehyde, 2- or 4-n-butylbenzaldehyde, 2-, 3- or 4-isopropylbenzaldehyde, 2- or 4-cyclopropylbenzaldehyde, 2,3-tetramethylenebenzaldehyde, 3,4-dioxymethylenebenzaldehyde, 2-, 3- or 4-methoxybenzaldehyde, 2-cyclopropylmethoxybenzaldehyde, 2-, 3- or 4-chloro-, -bromo- or -fluoro-benzaldehyde, 2-, 3- or 4-trifluoromethylbenzaldehyde, 2-, 3- or 4-trifluoromethoxybenzaldehyde, 2-, 3- or 4-difluoromethoxybenzaldehyde, 2-, 3- or 4-nitrobenzaldehyde, 2-, 3- or 4-cyanobenzaldehyde, 3-azidobenzaldehyde, 2-, 3- or 4-methylthiobenzaldehyde 2-, 3- or 4-methylsulphinylbenzaldehyde, 2-, 3- or 4-methylsulphonylbenzaldehyde, 2,3-, 2,4- or 2,6-dichlorobenzaldehyde, 2-fluoro-3-chlorobenzaldehyde, 2,4-dimethylbenzaldehyde, 2,4- or 2,6-dinitrobenzaldehyde, 2-chloro-6-nitrobenzaldehyde, 4-chloro-2-nitrobenzaldehyde, 2-nitro-4-methoxybenzaldehyde, 2-nitro-4-cyanobenzaldehyde, 2-chloro-4-cyanobenzaldehyde, 4-cyano-2-methylbenzaldehyde, 3-methyl-4-trifluoromethylbenzaldehyde, 3-chloro-2-trifluoromethylbenzaldehyde, thiophene-2-aldehyde, furan-2-aldehyde, pyrrole-2-aldehyde, pyrazole-4-aldehyde, imidazole-2-aldehyde, oxazole-2-aldehyde, isoxazole-3-aldehyde, thiazole-2-aldehyde, pyridine-2-, 3- or 4-aldehyde, 6-methylpyridine-2-aldehyde, 2-methylthio-pyridine-3-aldehyde, indole-3-aldehyde, benzimidazole-2-aldehyde, benzoxazole-4-aldehyde, benzoxadiazole-4-aldehyde, quinoline-4-aldehyde, quinazoline-2-aldehyde and quinoxaline-5-aldehyde.

Possible diluents are all the inert organic solvents. These include, preferably, alcohols, such as ethanol, methanol and isopropanol, ethers, such as dioxane, diethyl ether, tetrahydrofuran, glycol monomethyl ether and glycol dimethyl ether, and glacial acetic acid, dimethylformamide, dimethylsulphoxide, acetonitrile, pyridine and hexamethylphosphoric acid triamide.

The reaction temperatures can be varied within a substantial range. In general, the reaction is carried out between 20° and 150° C., but preferably at the boiling point of the particular solvent.

The reaction can be carried out under normal pressure, but also under increased pressure. In general, it is carried out under normal pressure.

In carrying out the process according to the invention, the substances participating in the reaction are in each case employed in molar amounts.

Process variant G

In process variant G, the leaving group L in 1,4-dihydropyridine derivatives of the general formula X

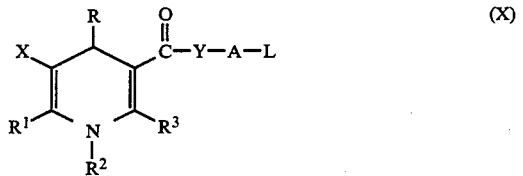

is replaced by the radical —ONO$_2$ or —ONO.

In the formula X, the radicals R, $R^1$, $R^2$, $R^3$, X, Y and A have the abovementioned meaning.

The leaving group L is above all halogen, especially chlorine, bromine or iodine.

The 1,4-dihydropyridine derivatives of the formula X used as starting substances are known from the literature, or they can be prepared by methods which are known from the literature (German Offenlegungsschrift (German Published Specification) No. 3,018,259).

Examples which may be mentioned are: 2-chloroethyl methyl 1,4-dihydro-2,6-dimethyl-4-(3-nitrophenyl)-pyridine-3,5-dicarboxylate, 2-bromoethyl isopropyl 1,4-dihydro-2,6-dimethyl-4-(3-nitrophenyl)-pyridine-3,5-dicarboxylate, 2-bromoethyl cyclopentyl 1,4-dihydro-2,6-dimethyl-4-(3-nitrophenyl)-pyridine-3,5-dicarboxylate, 2-iodoethyl decyl 1,4-dihydro-2,6-dimethyl-4-(3-nitrophenyl)-pyridine-3,5-dicarboxylate, 2-bromoethyl benzyl 1,4-dihydro-2,6-dimethyl-4-(3-nitrophenyl)-pyridine-3,5-dicarboxylate, bis-(2-iodoethyl) 1,4-dihydro-2,6-dimethyl-4-(3-nitrophenyl)-pyridine-3,5-dicarboxylate, 2-chloroethyl 2-methoxyethyl 1,4-dihydro-2,6-dimethyl-4-(2-trifluoromethylphenyl)-pyridine-3,5-dicarboxylate, 2-chloroethyl-2-phenoxyethyl 1,4-dihydro-2,6-dimethyl-4-(2-chlorophenyl)-pyridine-3,5-dicarboxylate, 2-bromoethyl methyl 1,4-dihydro-2,6-dimethyl-4-(2,3-dichlorophenyl)-pyridine-3,5-dicarboxylate, 2-bromoethyl isopropyl 1,4-dihydro-2,6-dimethyl-4-(2,1,3-benzoxadiazol-4-yl)-pyridine-3,5-dicarboxylate and 2-bromoethyl ethyl 1,4-dihydro-2,6-dimethyl-4-(2,1,3-benzoxadiazol-4-yl)-pyridine-3,5-dicarboxylate.

Inorganic nitrates or nitrites, preferably silver nitrate, silver nitrite or mercury-I nitrate, are used as reactants, and the salts can be employed in up to a five-fold molar excess.

The reaction can be carried out either in a heterogeneous phase system or in a homogeneous phase system.

Possible diluents are all the inert organic solvents. These include, preferably, alcohols, such as ethanol, methanol and isopropanol, ethers, such as dioxane, diethyl ether, tetrahydrofuran, glycol monomethyl ether and glycol dimethyl ether, and dimethylformamide, dimethylsulphoxide, acetonitrile, pyridine and hexamethylphosphoric acid triamide.

The reaction temperatures can be varied within a substantial range. In general, the reaction is carried out between 20° and 150° C., but preferably at the boiling point of the particular solvent.

The reaction can be carried out under normal pressure, but also under increased pressure. It is generally carried out under normal pressure.

The above preparation processes are given only for illustration, and the preparation of the compounds of the formula (I) is not restricted to these processes, but any modification of these processes is applicable in the same manner to the preparation of the compounds according to the invention.

Depending on the choice of starting substances, the compounds according to the invention can exist in stereoisomeric forms which either are mirror images (enantiomers) or are not mirror images (diastereomers). The present invention relates both to the antipodes and to the racemforms, and also the diastereomer mixtures. The racemic forms, like the diastereomers, can be separated into the stereoisomerically pure constituents in a known manner (compare, for example, E. L. Eliel, Stereochemistry of Carbon Compounds, McGraw Hill, 1962).

The following active compounds according to the invention may be mentioned, in addition to the preparation examples given below: ethyl 2-nitro-oxyethyl 1,4-dihydro-2,6-dimethyl-4-(2-nitrophenyl)-pyridine-3,5-dicarboxylate, isopropyl 2-nitro-oxyethyl 1,4-dihydro-2,6-dimethyl-4-(2-nitrophenyl)-pyridine-3,5-dicarboxylate, 2-(N-benzyl-N-methylamino)-ethyl 2-nitro-oxyethyl 1,4-dihydro-2,6-dimethyl-4-(3-nitrophenyl)-pyridine-3,5-dicarboxylate, 1,4-dihydro-2,6-dimethyl-4-(3-nitrophenyl)-pyridine-3,5-dicarboxylic acid 3-(2-nitro-oxyethyl ester) 5-anilide, 1,4-dihydro-2,6-dimethyl-4-(3-nitrophenyl)-pyridine-3,5-dicarboxylic acid 5-methyl ester 3-(2-nitrooxyethyl)-amide, 1,4-dihydro-2,6-dimethyl-4-(2-trifluoromethylphenyl)-pyridine-3,5-dicarboxylic acid 5-isopropyl ester 3-(2-nitro-oxyethyl)-amide, 1,4-dihydro-2,6-dimethyl-4-(2,3-dichlorophenyl)-pyridine-3,5-dicarboxylic acid 5-ethyl ester 3-(2-nitro-oxyethyl)-amide, isopropyl 2-nitro-oxyethyl 1,4-dihydro-2,6-dimethyl-4-(2,1,3-benzoxadiazol-4-yl)-pyridine-3,5-dicarboxylate, 1,4-dihydro-2,6-dimethyl-4-(2,1,3-benzoxydiazol-4-yl)-pyridine-3,5-dicarboxylic acid 5-ethyl ester 3-(2-nitro-oxyethyl)-amide and 1,4-dihydro-2,6-dimethyl-4-(2,1,3-benzoxadiazol-4-yl)-pyridine-3,5-dicarboxylic acid 5-isopropyl ester 3-(2-nitro-oxyethyl)-amide.

The new compounds have a broad and diverse pharmacological action spectrum.

In detail, the following main actions could be demonstrated in animal experiments:

1. On parenteral, oral and perlingual administration, the compounds produce a distinct and long-lasting dilation of the coronary vessels. This action on the coronary vessels is intensified by a simultaneous nitrite-like effect of reducing the load on the heart.

They influence or modify heart metabolism in the sense of an energy saving.

2. The excitability of the stimulus formation and excitation conduction system within the heart is lowered, so that an antifibrillation action which can be demonstrated at therapeutic doses results.
3. The tone of the smooth muscle of the vessels is greatly reduced under the action of the compounds. This vascular-spasmolytic action can take place in the entire vascular system or can manifest itself more or less isolated in circumscribed vascular regions (such as, for example, the central nervous system). The compounds are therefore particularly suitable as cerebral therapeutics.
4. The compounds lower the blood pressure of the normotonic and hypertonic animals and can thus be used as antihypertensive agents.
5. The compounds have strongly muscular-spasmolytic actions, which manifest themselves on the smooth muscle of the stomach, the intestinal tract, the urogenital tract and the respiratory system.

On the basis of these properties, the compounds according to the invention are particularly suitable for the prophylaxis and therapy of acute and chronic ischaemic heart diseases in the broadest sense, for the therapy of high blood pressure and for the treatment of disorders in cerebral and peripheral blood flow.

The new active compounds can be converted in a known manner into the customary formulations, such as tablets, capsules, dragees, pills, granules, aerosols, syrups, emulsions, suspensions and solutions, using inert non-toxic, pharmaceutically suitable excipients or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or excipients, optionally with the use of emulsifiers and/or dispersing agents, and, for example when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silica and silicates) and sugars (for example raw sugar, lactose and glucose), emulsifiers (for example polyoxyethylene fatty acid esters, polyoxyethylene fatty alcohol ethers, alkylsulphonates and arylsulphonates), dispersing agents (for example lignin-sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, in particular perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl-sulphate and talc, can be co-used when making tablets. In the case of aqueous suspensions and/or elixirs which are intended for oral use, the active compounds can be mixed with various flavour-improving agents or colorants in addition to the abovementioned auxiliary substances.

In the case of parenteral use, solutions of the active compounds, employing suitable liquid excipients, can be used.

In general, it has proved advantageous, in the case of intravenous administration, to administer amounts of about 0.001 to 10 mg/kg, preferably about 0.05 to 5 mg/kg, of body weight daily to achieve effective results, and in the case of oral administration, the dosage is about 0.05 to 20 mg/kg, preferably 0.5 to 5 mg/kg, of body weight daily.

Nevertheless, it can at times be necessary to deviate from the amounts mentioned, and in particular to do so as a function of the body weight of the experimental animal or of the nature of the administration method, but also because of the species of animal and its individual behavior towards the medicament, and the nature of the formulation of the medicament and the time or interval over which the administration takes place. Thus it can suffice in some cases to manage with less than the abovementioned minimum amount, whilst in other cases the upper limit mentioned must be exceeded. Where relatively large amounts of administered, it can be advisable to divide these into several individual administrations over the course of the day. The same dosage range is envisaged for administration in human medicine. In this case, the above statements also apply in the general sense.

PREPARATION EXAMPLES

EXAMPLE 1

2-Nitro-oxyethyl 5-acetyl-1,4-dihydro-2,6-dimethyl-4-(3-nitrophenyl)-pyridine-3-carboxylate

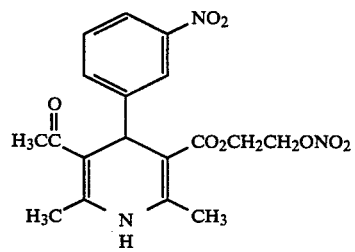

A solution of 14 g (36.9 mmols) of 2-chloroethyl 3-acetyl-1,4-dihydro-2,6-dimethyl-4-(3-nitrophenyl)-pyridine-3-carboxylate and 29.5 g (174 mmols) of silver nitrate in 220 ml of acetonitrile was stirred at 80° C. with exclusion of light for 2.5 hours. The silver chloride which has precipitated was filtered off with suction, the filtrate was concentrated in vacuo, the residue was taken up in methylene chloride and the mixture was washed briefly with ice-water. After drying over anhydrous sodium sulphate, the organic phase was concentrated under reduced pressure. The oily residue crystallized completely on trituration with a little ether, and the crude product was filtered off with suction and recrystallized from methanol.

Melting point: 125°-126° C., yield: 5.3 g (35%).

EXAMPLE 2

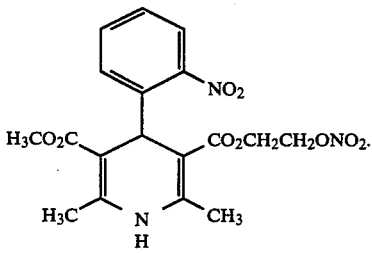

Methyl 2-nitro-oxyethyl 1,4-dihydro-2,6-dimethyl-4-(2-nitrophenyl)-pyridine-3,5-dicarboxylate of melting point 115° C. was obtained in a yield of 40% of theory analogously to Example 1 by reacting methyl 2-chloroethyl 1,4-dihydro-2,6-dimethyl-4-(2-nitrophenyl)-pyridine-3,5-dicarboxylate with silver nitrate in acetonitrile.

EXAMPLE 3

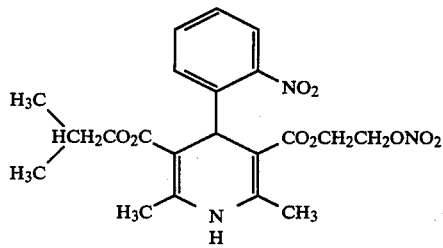

Isobutyl 2-nitro-oxyethyl 1,4-dihydro-2,6-dimethyl-4-(2-nitrophenyl)-pyridine-3,5-dicarboxylate of melting point 126° C. (isopropanol) was obtained analogously to Example 1 by reacting isobutyl 2-chloroethyl 1,4-dihydro-2,6-dimethyl-4-(2-nitrophenyl)-pyridine-3,5-dicarboxylate with silver nitrate in acetonitrile. Yield: 45% of theory.

EXAMPLE 4

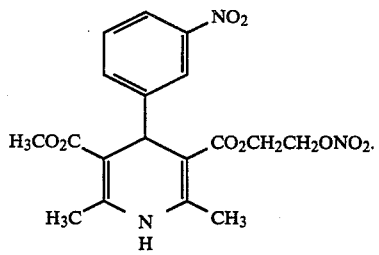

Methyl 2-nitro-oxyethyl 1,4-dihydro-2,6-dimethyl-4-(3-nitrophenyl)-pyridine-3,5-dicarboxylate of melting point 125° C. (methanol) was obtained analogously to Example 1 by reacting methyl 2-chloroethyl 1,4-dihydro-2,6-dimethyl-4-(3-nitrophenyl)-pyridine-3,5-dicarboxylate with silver nitrate in acetonitrile. Yield: 28% of theory.

EXAMPLE 5

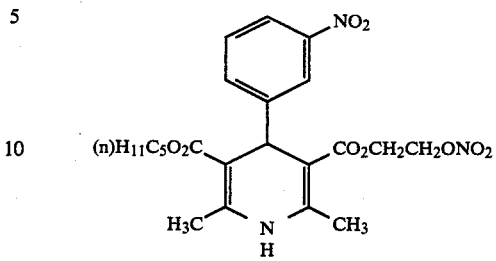

Pentyl 2-nitro-oxyethyl 1,4-dihydro-2,6-dimethyl-4-(3-nitrophenyl)-pyridine-3,5-dicarboxylate of melting point 102° C. was obtained analogously to Example 1 by reacting pentyl 2-chloroethyl 1,4-dihydro-2,6-dimethyl-4-(3-nitrophenyl)-pyridine-3,5-dicarboxylate with silver nitrate in acetonitrile. Yield: 33% of theory.

EXAMPLE 6

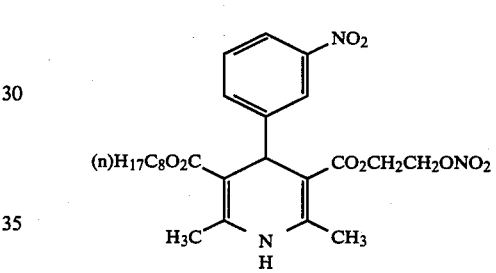

Octyl 2-nitro-oxyethyl 1,4-dihydro-2,6-dimethyl-4-(3-nitrophenyl)-pyridine-3,5-dicarboxylate of melting point 96° C. was obtained analogously to Example 1 by reacting octyl 2-chloroethyl 1,4-dihydro-2,6-dimethyl-4-(3-nitrophenyl)-pyridine-3,5-dicarboxylate with silver nitrate in acetonitrile. Yield: 25% of theory.

EXAMPLE 7

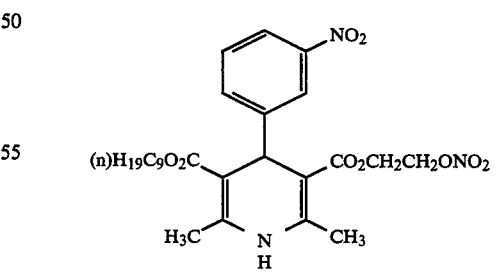

Nonyl 2-nitro-oxyethyl 1,4-dihydro-2,6-dimethyl-4-(3-nitrophenyl)-pyridine-3,5-dicarboxylate of melting point 89° C. was obtained analogously to Example 1 by reacting nonyl 2-chloroethyl 1,4-dihydro-2,6-dimethyl-4-(3-nitrophenyl)-pyridine-3,5-dicarboxylate with silver nitrate in acetonitrile. Yield: 31% of theory.

EXAMPLE 8

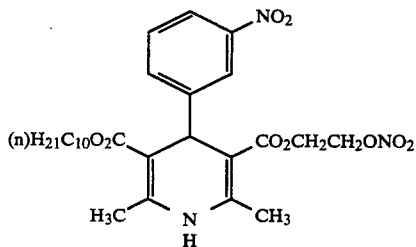

Decyl 2-nitro-oxyethyl 1,4-dihydro-2,6-dimethyl-4-(3-nitrophenyl)-pyridine-3,5-dicarboxylate of melting point 96° C. was obtained analogously to Example 1 by reacting decyl 2-chloroethyl 1,4-dihydro-2,6-dimethyl-4-(3-nitrophenyl)-pyridine-3,5-dicarboxylate with silver nitrate in acetonitrile. Yield: 22% of theory.

EXAMPLE 9

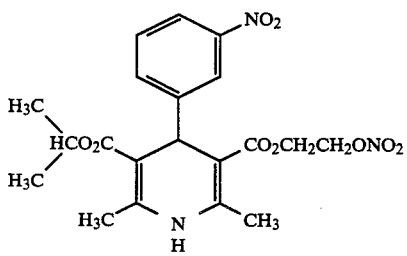

Isopropyl 2-nitro-oxyethyl 1,4-dihydro-2,6-dimethyl-4-(3-nitrophenyl)-pyridine-3,5-dicarboxylate of melting point 130° C. was obtained analogously to Example 1 by reacting isopropyl 2-bromoethyl 1,4-dihydro-2,6-dimethyl-4-(3-nitrophenyl)-pyridine-3,5-dicarboxylate with silver nitrate in acetonitrile. Yield: 36% of theory.

EXAMPLE 10

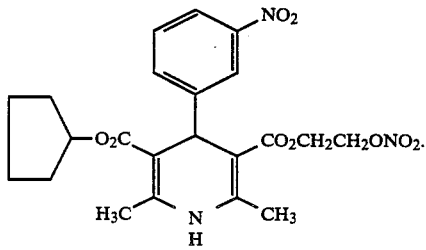

Cyclopentyl 2-nitro-oxyethyl 1,4-dihydro-2,6-dimethyl-4-(3-nitrophenyl)-pyridine-3,5-dicarboxylate of melting point 140° C. was obtained analogously to Example 1 by reacting cyclopentyl 2-chloroethyl 1,4-dihydro-2,6-dimethyl-4-(3-nitrophenyl)-pyridine-3,5-dicarboxylate with silver nitrate in acetonitrile. Yield: 39% of theory.

EXAMPLE 11

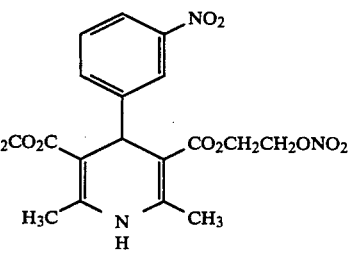

2-Methoxyethyl 2-nitro-oxyethyl 1,4-dihydro-2,6-dimethyl-4-(3-nitrophenyl)-pyridine-3,5-dicarboxylate of melting point 118° C. was obtained analogously to Example 1 by reacting 2-methoxyethyl 2-chloroethyl 1,4-dihydro-2,6-dimethyl-4-(3-nitrophenyl)-pyridine-3,5-dicarboxylate with silver nitrate in acetonitrile. Yield: 48% of theory.

EXAMPLE 12

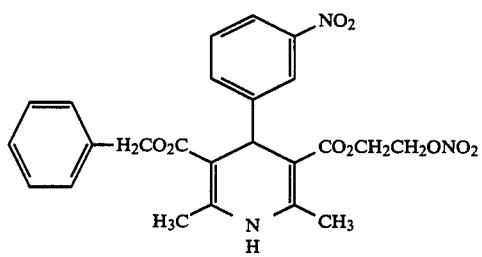

Benzyl 2-nitro-oxyethyl 1,4-dihydro-2,6-dimethyl-4-(3-nitrophenyl)-pyridine-3,5-dicarboxylate of melting point 137° C. was obtained analogously to Example 1 by reacting benzyl 2-chloroethyl 1,4-dihydro-2,6-dimethyl-4-(3-nitrophenyl)-pyridine-3,5-dicarboxylate with silver nitrate in acetonitrile. Yield: 34% of theory.

EXAMPLE 13

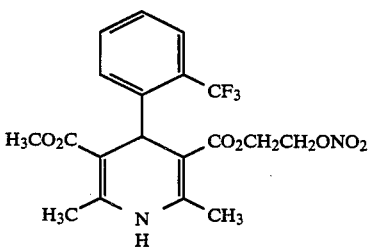

Methyl 2-nitro-oxyethyl 1,4-dihydro-2,6-dimethyl-4-(2-trifluormethylphenyl)-pyridine-3,5-dicarboxylate was obtained analogously, to Example 1 by reacting methyl 2-chloroethyl 1,4-dihydro-2,6-dimethyl-4-(2-trifluoromethylphenyl)-pyridine-3,5-dicarboxylate with silver nitrate in acetonitrile. Yield 34% of theory.

EXAMPLE 14

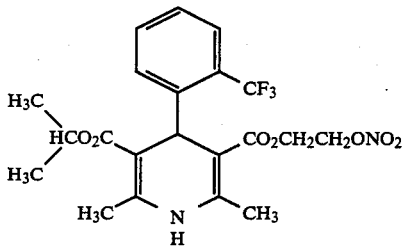

Isopropyl 2-nitro-oxyethyl 1,4-dihydro-2,6-dimethyl-4-(2-trifluoromethylphenyl)-pyridine-3,5-dicarboxylate of melting point 114° C. was obtained analogously to Example 1 by reacting isopropyl 2-chloroethyl 1,4-dihydro-2,6-dimethyl-4-(2-trifluoromethylphenyl)-pyridine-3,5-dicarboxylate with silver nitrate in acetonitrile. Yield: 29% of theory.

It is understood that the specification and examples are illustrative but not limitative of the present invention and that other embodiments within the spirit and scope of the invention will suggest themselves to those skilled in the art.

We claim:

1. A 1,4-dihydropyridine of the formula

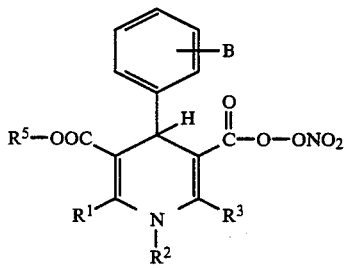

in which

B represents nitro or $CF_3$, $R^1$ and $R^3$, which can be identical or different, denote hydrogen, a straight-chain or branched alkyl radical with 1 to 4 carbon atoms, a phenyl radical or a benzyl radical, $R^2$ represents a hydrogen atom or a straight-chain or branched alkyl radical with 1 to 8 carbon atoms, the alkyl radical optionally being interrupted in the alkyl chain by an oxygen atom, or a phenyl radical or a benzyl radical, A represents a straight-chain or branched alkylene radical, $R^5$ represents a cyclic hydrocarbon radical which has from 5 to 20 carbon atoms, or a pharmaceutically acceptable acid addition salt thereof.

2. A dihydropyridine according to claim 1, wherein such dihydropyridine is cyclopentyl 2-nitro-oxyethyl 1,4-dihydro-2,6-dimethyl-4-((3-nitrophenyl)-pyridine-3,5-dicarboxylate of the formula

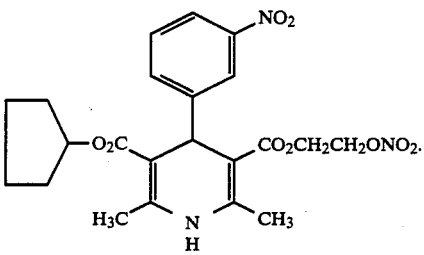

or a pharmaceutically acceptable acid addition salt thereof.

3. An antihypertensive composition of matter comprising an amount of a dihydropyridine or salt according to claim 1 effective in the treatment of hypertension in admixture with a pharmaceutically acceptable diluent.

4. A unit dose of a composition according to claim 3 in the form of a tablet, capsule or ampule.

5. A method of lowering the blood pressure of a patient which comprises administering to such patient an amount effective therefor of a dihydropyridine or salt according to claim 1.

6. A 1,4-dihydropyridine of the formula

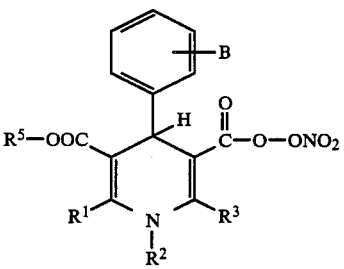

in which

B represents nitro or $CF_3$, $R^1$ and $R^3$, which can be identical or different, denote hydrogen, a straight-chain or branched alkyl radical with 1 to 4 carbon atoms, a phenyl radical or a benzyl radical, $R^2$ represents a hydrogen atom or a straight-chain or branched alkyl radical with 1 to 8 carbon atoms, the alkyl radical optionally being interrupted in the alkyl chain by an oxygen atom, or a phenyl radical or a benzyl radical, A represents a straight-chain or branched alkylene radical, $R^5$ represents a saturated or unsaturated hydrocarbon radical which has up to 20 carbon atoms and is interrupted in the chain by an oxygen atom, or a pharmaceutically acceptable acid addition salt thereof.

7. A dihydropyridine according to claim 6, wherein such dihydropyridine is 2-methoxyethyl 2-nitrooxyethyl 1,4-dihydro-2,6-dimethyl-4-((3-nitrophenyl)-pyridine-3,5-dicarboxylate of the formula

[Structure: 4-(3-nitrophenyl)-1,4-dihydro-2,6-dimethylpyridine-3,5-dicarboxylate with H3COH2CH2CO2C— and —CO2CH2CH2ONO2 groups]

or a pharmaceutically acceptable acid addition salt thereof.

8. An antihypertensive composition of matter comprising an amount of a dihydropyridine or salt according to claim 6 effective in the treatment of hypertension in admixture with a pharmaceutically acceptable diluent.

9. A unit dose of a composition according to claim 7 in the form of a tablet, capsule or ampule.

10. A method of lowering the blood pressure of a patient which comprises administering to such patient an amount effective therefor of a dihydropyridine or salt according to claim 6.

11. A 1,4-dihydropyridine of the formula

[Structure: 1,4-dihydropyridine with CF3-substituted phenyl at 4-position, X and —C(O)—O—A—ONO2 at 3,5-positions, $R^1$ and $R^3$ at 2,6-positions, $R^2$ on N]

in which

B represents nitro or $CF_3$, $R^1$ and $R^3$, which can be identical or different, denote hydrogen, a straight-chain or branched alkyl radical with 1 to 4 carbon atoms, a phenyl radical or a benzyl radical, $R^2$ represents a hydrogen atom or a straight-chain or branched alkyl radical with 1 to 8 carbon atoms, the alkyl radical optionally being interrupted in the alkyl chain by an oxygen atom, or a phenyl radical or a benzyl radical, A represents a straight-chain or branched alkylene radical, X represents the group —$COR^4$,
wherein $R^4$ represents a straight-chain or branched alkyl radical with 1 to 4 carbon atoms, or X represents the group —$COOR^5$,
wherein $R^5$ represents an alkyl radical which has up to 20 carbon atoms and is optionally interrupted by oxygen, or a pharmaceutically acceptable acid addition salt thereof.

12. A dihydropyridine according to claim 11, wherein such dihydropyridine is methyl 2-nitrooxyethyl 1,4-dihydro-2,6-dimethyl-4-(2-trifluoromethylphenyl)-pyridine-3,5-dicarboxylate of the formula

[Structure: methyl 2-nitrooxyethyl 1,4-dihydro-2,6-dimethyl-4-(2-trifluoromethylphenyl)-pyridine-3,5-dicarboxylate]

or a pharmaceutically acceptable acid addition salt thereof.

13. A dihydropyridine according to claim 11, wherein such dihydropyridine is isopropyl 2-nitrooxyethyl 1,4-dihydro-2,6-dimethyl-4-(2-trifluoromethylphenyl)-pyridine-3,5-dicarboxylate of the formula

[Structure: isopropyl 2-nitrooxyethyl 1,4-dihydro-2,6-dimethyl-4-(2-trifluoromethylphenyl)-pyridine-3,5-dicarboxylate]

or a pharmaceutically acceptable acid addition salt thereof.

14. An antihypertensive composition of matter comprising an amount of a dihydropyridine or salt according to claim 11 effective in the treatment of hypertension in admixture with a pharmaceutically acceptable diluent.

15. A unit dose of a composition according to claim 14 in the form of a tablet, capsule or ampule.

16. A method of lowering the blood pressure of a patient which comprises administering to such patient an amount effective therefor of a dihydropyridine or salt according to claim 11.

* * * * *